United States Patent
Hossack et al.

(10) Patent No.: US 7,670,290 B2
(45) Date of Patent: *Mar. 2, 2010

(54) ELECTRIC CIRCUIT FOR TUNING A CAPACITIVE ELECTROSTATIC TRANSDUCER

(75) Inventors: John A. Hossack, Charlottesville, VA (US); Brett Bymaster, Iowa City, IA (US); Igal Ladabaum, San Carlos, CA (US); Paul A. Wagner, El Cerrito, CA (US); Christopher M. W. Daft, Pleasanton, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1504 days.

This patent is subject to a terminal disclaimer.

(21) Appl. No.: 10/803,808

(22) Filed: Mar. 17, 2004

(65) Prior Publication Data

US 2004/0267134 A1   Dec. 30, 2004

Related U.S. Application Data

(63) Continuation of application No. 10/222,002, filed on Aug. 14, 2002, now Pat. No. 6,726,626.

(51) Int. Cl.
A61B 8/00    (2006.01)
(52) U.S. Cl. ............ 600/437; 600/438; 600/459; 310/309
(58) Field of Classification Search ............ 600/437, 600/438, 440, 442, 443, 447, 459; 310/309, 310/317, 334, 318
See application file for complete search history.

(56) References Cited

U.S. PATENT DOCUMENTS

| | | | |
|---|---|---|---|
| 3,243,743 A * | 3/1966 | Sziklai | 334/78 |
| 3,739,299 A | 6/1973 | Adler | |
| 4,790,021 A * | 12/1988 | Pribyl | 381/191 |
| 5,675,296 A | 10/1997 | Tomikawa | |
| 6,461,299 B1 | 10/2002 | Hossack | |
| 6,726,626 B1 * | 4/2004 | Hossack | 600/437 |
| 7,319,763 B2 * | 1/2008 | Bank et al. | 381/77 |

* cited by examiner

*Primary Examiner*—Brian Casler
*Assistant Examiner*—Amanda Lauritzen

(57) ABSTRACT

An electrostatic transducer circuit and method of tuning the same, in which a balancing circuit is inserted into the electrostatic transducer circuit, is described. The electrostatic transducer circuit generally includes transmit circuitry, receive circuitry, a capacitive electrostatic transducer and the balancing circuit. The balancing circuit can include, either singly or in combination, an inductance and a negative capacitance. The balancing inductance is tuned to counteract the negative reactance of the capacitive electrostatic transducer at a desired operating frequency and can be inserted into the transmit circuitry and/or the receive circuitry. The balancing negative capacitance is tuned to counteract the capacitance of the capacitive electrostatic transducer and can be inserted into the receive circuitry and/or the transmit circuitry. The transmit circuitry can be isolated from the receive circuitry, and vice versa, once the balancing circuit has been inserted. Isolation can be achieved by switching the electrostatic transducer circuit between transmit and receive modes of operation, or by providing separate transmit and receive electrode subsets.

37 Claims, 14 Drawing Sheets

Type 2 Negative Capacitor

Type 1 Negative Capacitor

ELECTRIC CIRCUIT FOR TUNING A CAPACITIVE ELECTROSTATIC TRANSDUCER

CROSS-REFERENCE TO RELATED APPLICATIONS

This application is a continuation-in-part of, and claims the benefit of priority from, U.S. patent application Ser. No. 10/222,002 filed on Aug. 14, 2002 to John A. Hossack and entitled "Electric Circuit for Tuning a Capacitive Electrostatic Transducer" (now U.S. Pat. No. 6,726,626 B1, issued on Apr. 27, 2004), which is fully incorporated herein by reference for all purposes.

BACKGROUND OF THE INVENTION

1. Field of the Invention

The present invention generally relates to the field of electro-acoustic transducer circuits. More specifically, the present invention relates to tuning circuitry for capacitive electrostatic microfabricated electro-acoustic transducers.

2. Description of the Related Art

An electro-acoustic transducer is an electronic device used to emit and receive sound waves. These transducers are used in medical imaging, non-destructive evaluation and other applications. Ultrasonic transducers are electro-acoustic transducers that operate at higher frequencies, typically at frequencies exceeding 20 kHz.

The most commonly used type of ultrasonic transducer is the piezoelectric transducer (PZT) made of ceramic materials. In recent years, a revolutionary, new technology has been developed with the potential of displacing conventional piezoelectric ceramic-based ultrasound transducers used for medical ultrasound imaging. These new transducers are made of fine microfabricated membranes suspended above Silicon-based substrates. These transducers operate in an electrostatic mode and electrically approximate a parallel-plate capacitor with finely spaced plates. These microfabricated transducers have considerable potential since the microfabrication process gives rise to low cost, highly complex structures—such as finely pitched 2D arrays of elements. Furthermore, since the microfabricated transducers are based on Silicon, it is envisioned that suitable driver and receiver circuitry may be integrated onto the same Silicon substrate or onto one immediately adjacent to the transducer substrate. Thus, the microfabrication technology may enable 2D arrays and real-time 3D imaging, which until now has been hampered by the cost and complexity of the cumbersome, time consuming, low-yield manufacturing processes required for the ceramic-based arrays. The microfabrication technology may also enable new intravascular applications such as placing transducer arrays on the tips of catheters or on other temporary, or semi-permanent, minimally invasive monitoring instrumentation used inside the body to monitor physiological functions (e.g., blood flow, blood pressure, etc.).

One drawback of the electrostatic microfabricated transducer arrays is that they substantially behave with the electrical characteristics of a capacitor. The capacitance of the microfabricated transducer introduces a negative reactance component to the overall transducer impedance, which makes the transducer inefficient. What is needed is a way to tune out the negative reactance of the microfabricated transducer. Further still, the practical constraints of making connections to the microfabricated transducer can introduce sources of parasitic capacitance that, in addition to the transducers intrinsic capacitance, add to the negative reactance of the impedance. Thus, it is also desirable to tune out parasitic components of the transducer assembly's capacitance.

A typical imaging probe used, for example, in harmonic imaging has between about 128 and 192 channels. Each transducer associated with this typical imaging probe operates in two directions (e.g., transmit and receive), or as is know in the art, in a pulse-echo fashion. Each transmit and receive pair operates using the same path signal path, typically a coax path (e.g., 192 coax paths for the 192 channel probe). The transmit voltages of such systems can be large, on the order of +/−100V, and are very short in duration, for example, 1 cycle of a 5-10 MHz sine or square wave. The receive voltages of such systems can be quite small, on the order of 100 mV down to less than 1 mV. To ensure the desired probe quality, receive sensitivity is an important design constraint, so low noise components are better. Any active circuitry attached to the transducer should be protected from large transmit voltages, while at the same time should be able to switch quickly into a highly sensitive receive mode (e.g., within about ½ μsec for the typical system).

The capacitive electrostatic transducer of the typical probe is a capacitive sensor that, when biased with a DC potential, acts as a transformer between the electrical and acoustic domains. The electrical impedance of this transducer can be dominated by a capacitive component on the order of 20-200 pF, which also contains a resistive part that varies with frequency and has real to imaginary ratios on the order of about 1:4 to 1:15 or more. FIG. 1 illustrates the complex series impedance vs. frequency plots for such a transducer.

The effect of a relatively large imaginary part compared to the real part of the transducer is that it can make transduction inefficient and it can cause reflections in the electrical and the acoustic domains. For example, it is typical for a coaxial cable to connect each active transduction element in the probe to the ultrasound system. Such cables have typical impedance ranges of 50 to 75 Ohms. A transmit signal traveling from the system to the probe tip on such a cable encounters the complex series impedance of FIG. 1. If the absolute magnitude of the complex impedance does not match the cable impedance, a reflection of the signal will bounce back toward the system. Furthermore, the voltage established across the transducer's impedance will be apportioned between the real and the imaginary part of the impedance. Only the real part of the impedance corresponds to the actual output of ultrasound in the medium of interest, so if the imaginary part is relatively large, only a small fraction of the transmit voltage is available for sound transmission.

From the acoustic domain's perspective, an ultrasound wave traveling in the medium (for example, the human body) toward the transducer will be partially reflected unless the acoustic impedance presented by the transducer is identical to that of the medium. Acoustic reflections are undesirable for two reasons. First, a reflection implies that not all of the power in the acoustic wave is being converted into an electrical signal, so transduction is not efficient. Second, and of particular importance in imaging applications, reflections from the transducer surface can manifest themselves as reverberation, or ghost images. A reflection from the transducer surface is in effect a false transmit event.

From systems theory, it can be demonstrated that a transducer will present a impedance matched to the medium if it is electrically connected to a receive circuit with an input impedance equal to the complex conjugate of the transducer's electrical impedance when loaded by the medium of interest. Thus, what is needed is electrical circuitry for presenting the desired impedance to the probe transducers.

It is possible, as shown in the embodiment of FIG. 5, to generate an impedance that looks like a negative reactance using passive components. However, passive designs are practical over a relatively narrow range of frequencies. Thus, what is needed is active circuitry for presenting a negative capacitance load to the probe transducers. As may be evident to those skilled in the art, negative capacitance circuits can lead to unstable conditions; it is desirous to achieve a negative capacitance that follows the transducer capacitance as closely as possible without inducing instability in the probe.

Furthermore, the active receive circuitry needs to be protected from the transmit signal. One approach is to switch the negative capacitor out of the circuit on transmit, and then switch it back immediately after transmit in preparation for receive. However, typical approaches for such protection circuitry require high voltage components given the +/−100 V transmit pulse.

In order to enable small probe packages and to limit the parasitic capacitance that loads the transducer on receive, it is desirable to provide active circuitry that in the form of an integrated circuit. However, low noise integrated circuit processes that are viable candidates for negative capacitor and pre-amplification circuits are not usable for high voltage protection circuitry. Thus, what is needed are electric circuit and transducer topologies such that low noise, low voltage integrated receive circuits can withstand transmit voltages.

Ultimately what is needed is a solution to the problem for operating a capacitive microfabricated transducer efficiently and with reduced acoustic reflectivity.

SUMMARY OF THE INVENTION

The present invention includes embodiments for tuning out, or balancing, the negative reactance of a capacitive microfabricated electrostatic transducer. The negative reactance can be tuned out, for example, by using inductive tuning, thereby making the transducer circuit more efficient. The capacitance can be balanced, for example, by inserting a negative capacitor into the receive signal path. The inductive tuning of some embodiments of the present invention result in a capacitive microfabricated electrostatic transducer that is efficient for harmonic imaging.

The present invention provides an electrostatic transducer circuit in which a balancing circuit is inserted into an electrostatic transducer circuit. The electrostatic transducer circuit generally includes a transmit signal path, a receive signal path, a capacitive electrostatic transducer and the balancing circuit. In some embodiments, the transmit and receive signal paths can be combined. The balancing circuit can include inductance that is tuned to counteract the negative reactance of the capacitive electrostatic transducer at a desired operating frequency. The balancing circuit can also include, either alone or in combination with the inductance, a negative capacitor formed, for example, from active components such as an op-amp or transistors, to balance the capacitance of the capacitive electrostatic transducer. The balancing reactance can be inserted into the transmit circuitry during the transmit mode, or into the receive circuitry during the receive mode (or both) and can be isolated from the remaining parts of the electrostatic transducer circuit (i.e., the receive from transmit and vice versa). Isolation can be achieved by switching the electrostatic transducer circuit between transmit and receive modes of operation. Likewise, the negative capacitor can be inserted into the receive circuitry and can be switched for isolation during transmission. Further, the negative capacitor can be inserted into the receive circuitry in such a manner that it is not effected by high voltage transmit signals.

BRIEF DESCRIPTION OF THE DRAWINGS

These and other aspects and features of the present invention will become apparent to those ordinarily skilled in the art upon review of the following description of specific embodiments of the invention in conjunction with the accompanying figures, wherein.

DETAILED DESCRIPTION OF THE INVENTION

Figure 1:
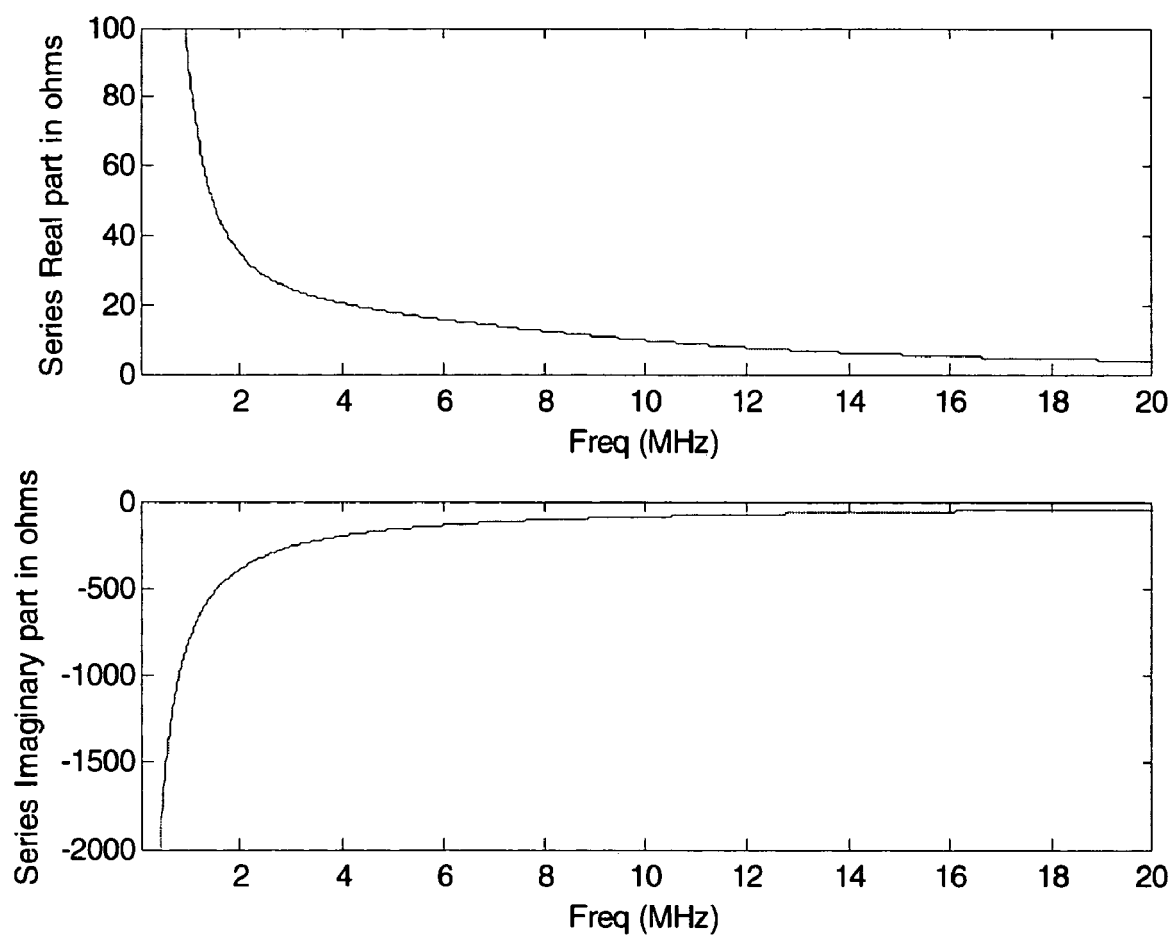
FIG. 1 illustrates the complex series impedance vs. frequency plots for such a transducer for use with a typical harmonic imaging probe.

The present invention will now be described in detail with reference to the drawings, which are provided as illustrative examples of the invention so as to enable those skilled in the art to practice the invention. Notably, the figures and examples below are not meant to limit the scope of the present invention. Where certain elements of the present invention can be partially or fully implemented using known components, only those portions of such known components that are necessary for an understanding of the present invention will be described, and detailed descriptions of other portions of such known components will be omitted so as not to obscure the invention. Further, the present invention encompasses present and future known equivalents to the components referred to herein by way of illustration.

According to an embodiment of the present invention, one aspect inserts a tuned balancing reactance into the transmit side of an electro-acoustic transducer circuit. The electro-acoustic transducer circuit of the present invention includes a capacitive electrostatic transducer. This embodiment tunes the balancing reactance to counteract the negative reactance of the capacitive electrostatic transducer at the desired operating frequency. The tuned balancing reactance of the present invention preferably uses an inductor. This balancing reactance may comprise a single series connected inductor. However, it may comprise additional components (e.g., additional inductor(s), transformer(s), etc.). This component (or these components) may be connected in series or in parallel or in combinations of series and parallel with respect to the capacitive transducer. The inductance in this embodiment may include a real resistive characteristic in addition to the pure imaginary reactance presented by a perfect inductor. This resistive characteristic may be included by design (possibly by a series or parallel resistor) or as a result of the imperfections that are found in practical inductors. Additionally, the embodiment isolates the balancing reactance from the receive circuit of the electro-acoustic transducer circuit. The isolation of the present invention includes switching between the transmit and receive circuits of the electro-acoustic transducer circuit using a switch. The present invention provides an improvement in sensitivity that assists in making the transducer performance more closely match, and possibly exceed, the performance of more conventional transducers used for these applications, such as PZT ceramic or polymer transducers.

The present invention is preferably used in the context of a high frequency, high channel count imaging array used for diagnostic imaging. The medium into which the capacitive electrostatic transducer is operated is typically tissue, which has an acoustic property that approximates water. Accordingly, the acoustic impedance of the acoustic membrane, described further herein, is very low compared to the impedance of the fluid. Thus, the capacitive electrostatic transducer circuit according to the present invention is substantially non-resonant when operated in tissue. And, since it is effectively non-resonant, it will have a large bandwidth. However, the electrical impedance near the frequency of interest includes a real part that may be on the order of 50-100 ohms, and a negative reactance, due to the capacitance of the transducer, on the order of several hundred to thousands of ohms. This high imaginary impedance restricts current flow into the capacitive electrostatic transducer.

The present invention will now be described in detail with reference to the accompanying drawings, which are provided as illustrative examples of embodiments of the present invention. Throughout the description of the various embodiments of the present invention, reference is made to transducer, capacitive microfabricated electrostatic transducer, ultrasonic electro-static transducer and the like. This terminology is merely exemplary. Those skilled in the art, taking into consideration the teachings of the present disclosure, will realize that the present invention can apply to a myriad of types of transducers, as well as various arrays of such transducers. These variations are intended to be within the scope of the present invention.

Figure 2:
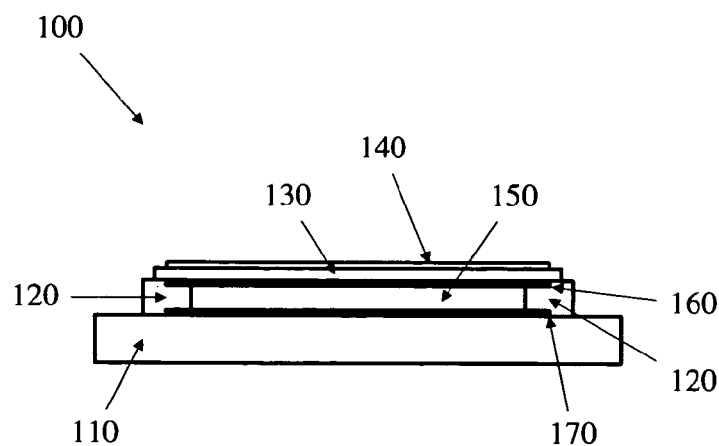
FIG. 2 illustrates a conventional capacitive microfabricated electrostatic transducer.

FIG. 2 illustrates a conventional capacitive microfabricated electrostatic transducer 100. The capacitive microfabricated electrostatic transducer 100 includes a substrate 110 that contains a lower conductive plate 170 formed on a top surface of the substrate 110. Insulating supports 120, formed from, for example, silicon dioxide, are formed over the lower conductive plate 170. The insulating supports 120 are spaced at peripheral locations around the perimeter of membrane 130 so as to cause the membrane 130 to be in tension above a separation 150. The membrane 130 further contains a conductive portion that forms an upper conductive plate 160. This results in the separation 150 being located between the lower conductive plate 170 and the upper conductive plate 160. Additionally, the membrane 130 contains at least one signal electrode 140, which is also electrically connected to the upper conductive plate 160. As is known, the separation 150 is typically obtained using a sacrificial layer that is applied and subsequently removed after formation of other layers thereover, although other techniques can be used. And it is understood that this capacitive microfabricated electrostatic transducer is described for background purposes, and that other types of microfabricated transducers fall within the scope of the present invention, as will become to those skilled in the art from the further teachings and descriptions provided hereinafter.

The present embodiment operates, however, within the context of a capacitive microfabricated electrostatic transducer, and, as such, the capacitive microfabricated electrostatic transducer illustrated in FIG. 2 will be used to describe the present invention.

Figure 3A:
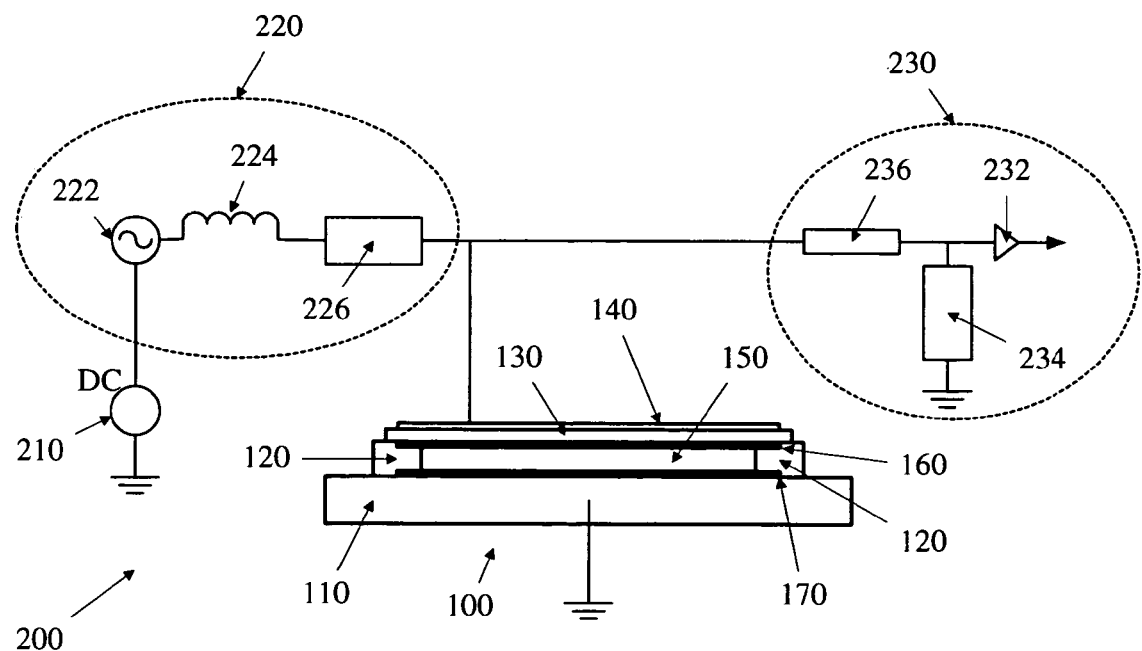
FIGS. 3A-3C illustrate a microfabricated capacitive electrostatic transducer with a switched balancing reactance according to an embodiment of the present invention.

FIG. 3A illustrates an embodiment of the present invention; a capacitive, microfabricated electrostatic transducer circuit 200, which includes a capacitive microfabricated electrostatic transducer 100, with elements as described above with reference to FIG. 2. Connected to at least one signal electrode 140 are the circuit components that will be described hereinafter, which allow for the capacitive microfabricated electrostatic transducer 100 to transmit and receive signals. The capacitive microfabricated electrostatic transducer circuit 200 also includes a switched balancing reactance 224, which, as described hereinafter, will allow for the balancing of the negative reactance of the capacitive element of the capacitive microfabricated electrostatic transducer 100 during a transmit mode.

The transmit circuitry 220 of the capacitive microfabricated electrostatic transducer circuit 200 includes a signal generator 222 that generates a transmit frequency drive voltage as appropriate for the application, and is selected in combination with the geometry of the various elements of the capacitive microfabricated electrostatic transducer 100. This drive voltage is preferably as small as possible, since that allows for many efficiencies to be gained both in terms of the signal generator 222 used, and the tolerance of the design of the capacitive microfabricated electrostatic transducer 100. The balancing reactance 224 is connected between the signal generator and a switching block 226. The balancing reactance 224 is chosen to have a value that counteracts the negative reactance of the capacitive electrostatic transducer 100 at a desired operating frequency. While the balancing reactance 224 is typically implemented as a series inductor, as is illustrated in FIG. 3A, it is noted that the balancing reactance 224 can also be implemented as parallel components, such as parallel inductors, a combination of either series or parallel components, or a combination of series and parallel components. It is also noted that if an electrical transformer is used in the transmit path, it will provide some inductance that may form all or part of the total inductance required for tuning out the negative reactance of the capacitive microfabricated electrostatic transducer 100.

Figure 3B:
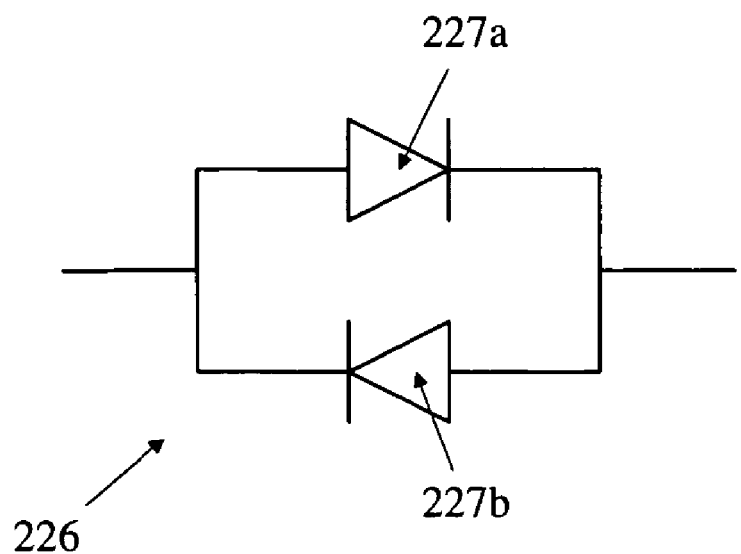

The switching block 226 is chosen so as to allow sufficiently fast switching between the transmit mode, during which the acoustic signal is generated by the capacitive electrostatic transducer 100, and the receive mode, during which reflected acoustic signals are detected by the capacitive electrostatic transducer 100. The switching block 226 can use diodes (illustrated in FIG. 3B), a multiplexer (see FIG. 3C), or other switching means. Generally the switching block 226 is solid state but can in principle be mechanical—including micro-machined mechanical switches. Depending on the configuration of the balancing reactance 224 the switching block 226 may operate in either a closed or open mode during transmit and the opposite mode (i.e. open or closed, respectively) during receive. In a more complex circuit involving a combination of parallel and series balancing components there may be more than one switching block and these switching blocks may operate in different switching modes (i.e. one may close after transmit and another may open after transmit). What is important is that the effect of the reactive balancing component(s) should be included in the circuit during transmit and isolated (or partially isolated) during receive. If diodes 227a & 227b are used as illustrated in FIG. 3B, opposite terminals of each diode can be connected together to form the switching block 226, such that each is in a forward bias state during one of the positive or negative portions of the transmit signal, and the existence of the diodes 227a & 227b isolates the impedance of the balancing reactance 224 from both the receive circuit 230 and the capacitive electrostatic transducer 100. If needed, the transmit circuit 220 can include provisions to compensate for any voltage drop across the switching block 226, such as the forward-bias voltage drop across a diode (typically about 0.7V) to each positive and negative portions of the signal waveform generated by the signal generator 222. Alternatively, if the switching block 226 is implemented as a multiplexer 228, as illustrated in FIG. 3C, a control line 229 is additionally needed to transmit a control signal that will cause switching between transmit circuitry 220 and receive circuitry 230, as shown.

The receive circuitry 230 includes a preamplifier 232 that initially amplifies signals received by the capacitive electrostatic transducer 100. The receive circuitry can also include filters, such as the filters 234 & 236 that are shown. The filters 234 & 236 provide filtering in the vicinity of the second harmonic of the transmitted frequency, where the transmitted frequency is related to the series resonant frequency of the capacitive electrostatic transducer 100 and the balancing reactance 224. For a further discussion of other considerations that are relevant to the overall operation of the receive circuit 230, but not the present invention as described herein, see the article entitled "Surface Micromachined Capacitive Ultrasonic Transducers" by Ladabaum et al, in IEEE Trans. EFFC Vol. 45, No. 3, May 1998.

The transmit circuitry 220 and the receive circuitry 230 can be formed as either part of the same semiconductor substrate 110 that is used to form the capacitive electrostatic transducer 100 or as a circuit that is separate from it. Preferably, however, at least the preamplifier 232 of the receive circuitry 230 is formed on the same semiconductor substrate 110 that is used to form the capacitive electrostatic transducer 100, as well as the balancing reactance 224. In particular, the balancing reactance 224, when used with a micromachined transducer, is implemented as a microinductor using, for example, techniques that have been described by Allen et al. at Georgia Tech. University in, "Micromachined Inductors with Electroplated Magnetically Anisotropic Alloy Cores" in Proceedings of the Fifth International Symposium on Magnetic Materials, Processes, and Device Applications to Storage and Microelectromechanical Systems (MEMS); Electrochem. Soc. 1999, pp 389-401 and "New Micromachined Inductors on Silicon Substrates," in IEEE Transactions on Magnetics, vol. 35. no. 5 pt 2. September 1999, p 3547-49. These components can be formed using conventional fabrication techniques, and a further description of their formation is not believed necessary.

Figure 3C:
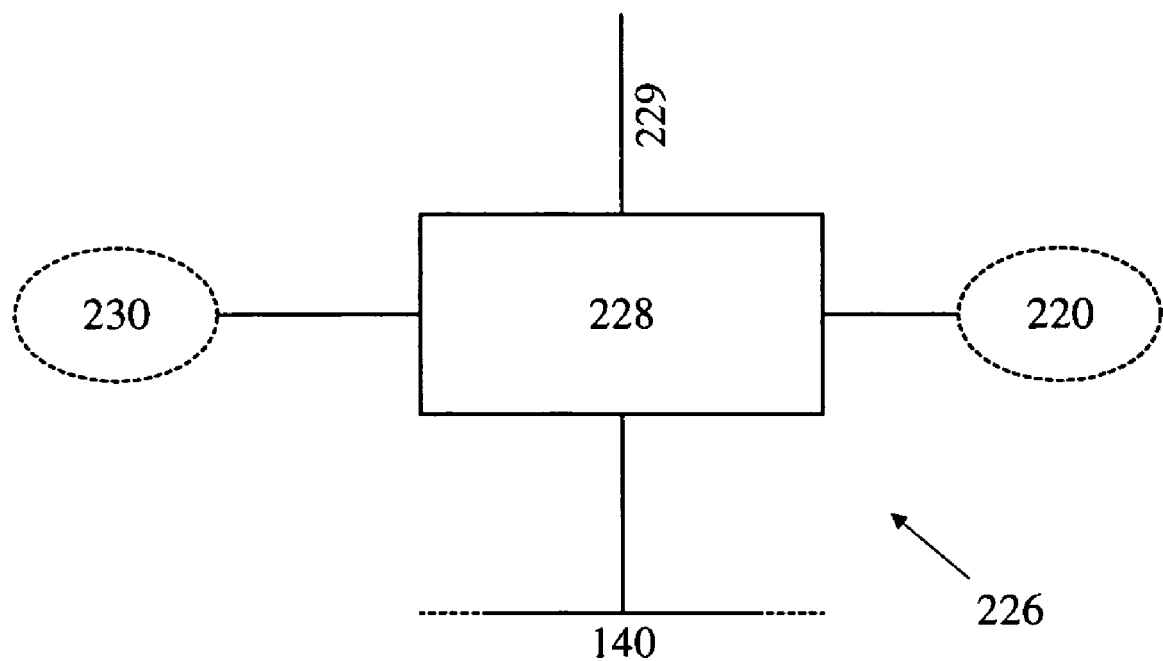

During transmission of the embodiment shown in FIGS. 3A-3C, the receive circuitry 230 is left connected to the capacitive microfabricated electrostatic transducer circuit 200. Whereas during reception, the transmit circuitry 220 is effectively disconnected from the transducer circuit 200 by switching block 226, and thus, the receive circuitry 230 is left untouched by the effects of the balancing reactance 224 in the transmit circuitry 220.

The basic operation of an embodiment of the present invention shown in FIG. 3A includes applying a DC bias voltage 210 to the capacitive electrostatic transducer 100. Initially, an acoustic signal is generated by generating a signal from the signal generator 222, which signal is tuned as a result of the balancing reactance 224 and drives the capacitive electrostatic transducer 100, thereby creating the acoustic signal that emanates therefrom at a frequency corresponding to the frequency of the transmit signal.

During a transmit mode, the capacitance of the capacitive electrostatic transducer 100 produces a negative reactance component that is counteracted by the positive reactance of the balancing reactance 224, which is selected for that purpose. The balancing reactance 224 should be selected to withstand the voltages and currents to which it is expected to be subjected.

When the capacitive electrostatic transducer 100 is in a receive mode and a reflected signal is thereafter received, the separation 150 as a function of time between the upper conductive plate 160 and the lower conductive plate 170 changes according to the received acoustic pressure function. This change in plate separation 150 causes a change in capacitance and this change in capacitance can be detected in one of several ways. For example, a DC voltage can be applied from a fixed DC source via a resistor. As the capacitance changes as a function of the received acoustic pressure, the capacitor impedance changes and hence the potential detected across the capacitor changes. Other more sophisticated approaches to measuring capacitance change exist. As one example, the method described by Ergun et al. in 'A New Detection Method for Capacitive Micromachined Ultrasonic Transducers' (IEEE Trans. UFFC Vol. 48, No. 4, pp. 932-942) may be suitable. The balancing reactance 224 is in the transducer circuit 200 only during the transmit pulse duration. In the case of a 2 MHz transducer, this transmit pulse may last on the order of 0.25 to 2.0 microseconds. The switching block 226 that isolates the balancing reactance 224 operates at some small interval after the end of the transmit pulse excitation. This switching block 226 operation may occur, for example, between 0.0 and 2.0 microseconds after the end of the transmit pulse. The switching block 226 may operate before the transducer has completely stopped vibrating as a result of the transmit excitation. However, the switching block 226 should operate before the first meaningful reflected signals are received. It is well known that the first instant after the transmit pulse, the transducer is subjected to 'main bang' effects that may saturate the receive circuitry 230. The timing of the switching block 226 operation and timing of a switch (if one is present) that switches in the receive circuitry 230 (which is normally 'protected' from the transmit waveform) may be subject to experimental or theoretical optimization in terms of useful received reflected signal. Hence, the average capacitance, C, of the capacitive electro-static transducer 100 is changed, as is apparent from the well-known formula $C=((\in *A)/D)$, where $\in$=dielectric constant of insulation between plates, A=area of plates, and D=plate separation.

This formula gives the average capacitance as the membrane is at rest. The capacitance will change slightly during vibration but the above calculation is sufficient for designing the preferred transducer circuit 200. Specifically, during transmit mode, the charge, Q, on the capacitive electrostatic transducer 100 is a function of the drive voltage obtained from the signal generator 222. During the receive mode, the acoustic signals received will cause a different vibration of the membrane 130, and, therefore, a change in capacitance from that which existed during the transmit mode. This changed capacitance is thus detected as the receive signal generated from the capacitive electro-static transducer 100, which receive signal is supplied via at least one signal electrode 140 to the preamplifier 232. It is noted that there are stray capacitance issues associated with the received signal that are known, and, as a result, they are not discussed further herein.

Figure 4:
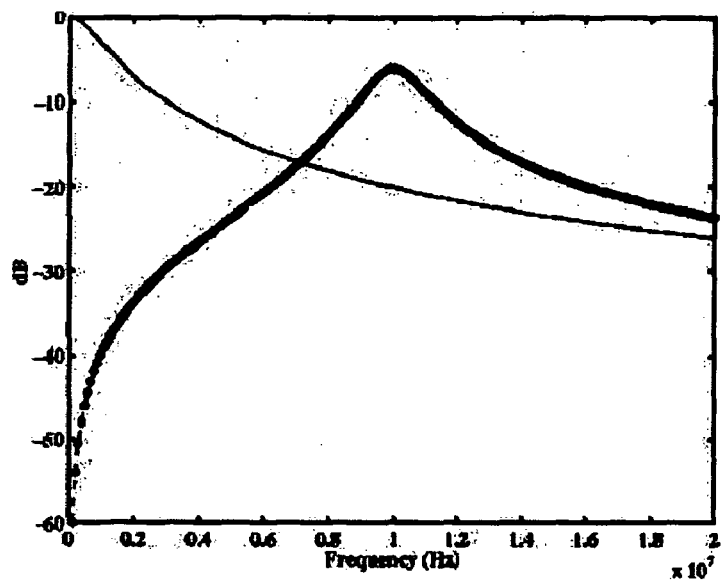
FIG. 4 illustrates the resulting improvement on voltage delivered to the real part of the transducer impedance according to and embodiment of the present invention.

To illustrate the reactance selection for this embodiment of the present invention, assume, as is known, that the typical resistance of a 10 MHz immersion (water use) electro-acoustic transducer is between 50 and 100 ohms. Capacitance at this resistance corresponds to approximately 15 pF, which is also approximately typical for certain transducer designs and known in the art. The series imaginary impedance for a capacitance of 15 pF is approximately −1000 ohms at a desired operating frequency of 10 MHz. Thus, without the balancing reactance of the embodiment of the present invention, the current available to the real part of the transducer impedance (which is responsible for energy conversion) is approximately 10% of its maximum. Therefore, as shown in FIG. 3A, this embodiment of the present invention inserts a balancing reactance 224, illustrated as a series inductor, with an impedance of +1000 imaginary ohms at 10 MHz to counteract the negative reactance of the capacitive electrostatic transducer 100 at a desired 10 MHz operating frequency. Under these exemplary conditions, this equates to inserting a 16 µH series inductor. FIG. 4 illustrates the resulting improvement on voltage delivered to the real part of the transducer impedance according to and embodiment of the present invention. At the exemplary desired operating frequency of 10 MHz, the delivered voltage is improved by more than 10 dB.

Figure 5:
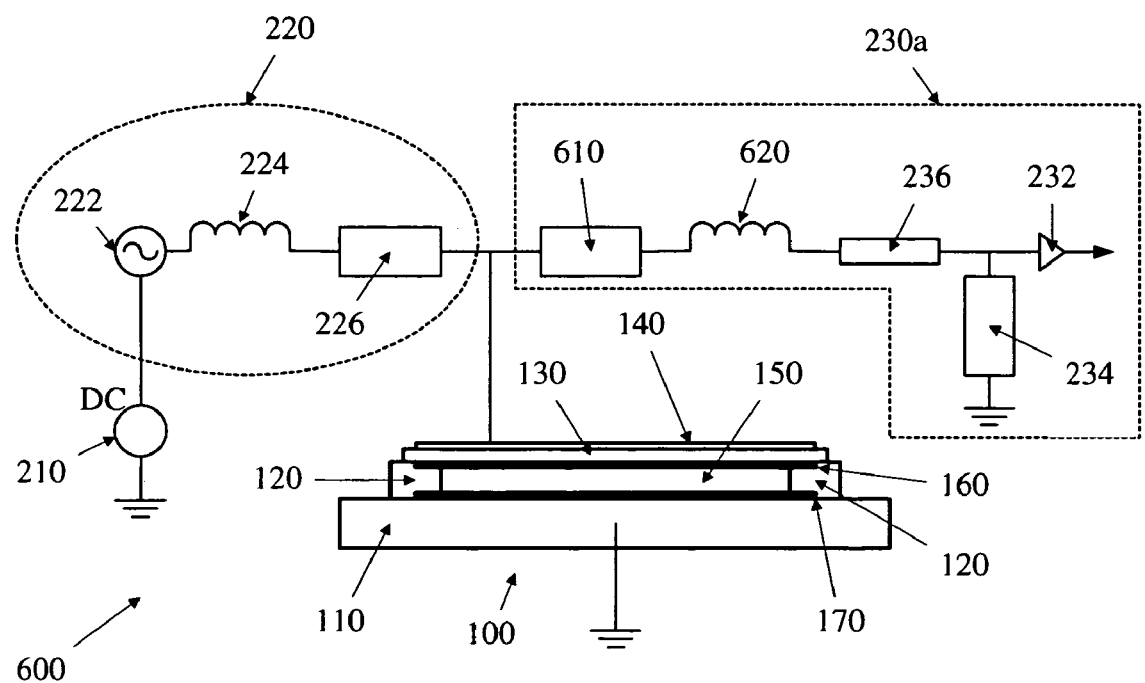
FIG. 5 illustrates a microfabricated capacitive electrostatic transducer with a switched balancing reactance according to another embodiment of the present invention.

Another embodiment of the present invention is shown in FIG. 5, and illustrates the further inclusion of a receive balancing reactance 620, also preferably implemented using a series inductor, and a receive switching block 610 inserted in the receive circuit 230a closest to the capacitive electrostatic transducer 100, with the other components of this alternate capacitive, microfabricated electrostatic transducer circuit 600 the same as the circuit 200 illustrated in FIG. 3A. This alternate circuit 600 would typically still include a balancing reactance 224 in the transmit circuit 220, which would still be selected to tune out the negative reactance of the capacitive electrostatic transducer during transmission.

The value of the receive balancing reactance 620 of this embodiment has a different value from the balancing reactance 224 of the transmit circuit 220, as described hereinafter, but would also be isolated from the transmit circuit 220 by the receive switching block 610, as illustrated, during a receive mode. The receive switching block 610 would be open during transmit (isolating the receive balancing reactance 620 from the transmit circuit 220) and closed during receive, so as to switch in the receive balancing reactance 620 during receive. The switching block 226 would operate as previously discussed and in an opposite mode to receive switching block 610—i.e. the switching block 226 would be closed during transmit so as to include the balancing reactance 224 but open during receive to isolate the balancing reactance 224 from the receive circuitry 230a. The receive switching block 610 can be made of the same types of components as is the switching block 226 previously described, such as with reference to FIGS. 3B and 3C.

As an example of selecting the receive balancing reactance 620, assume the same conditions provided in the previous example above, except assume the desired operating frequency is 20 MHz—the 'second' harmonic of the 10 MHz transmit center frequency ('first' harmonic or 'fundamental'). With an electrostatic transducer capacitance of 15 pF, the receive circuit 230a receive balancing reactance 620 of this embodiment would preferably be 4.2 µH. As with the embodiment discussed above, the receive balancing reactance 620 can also be implemented as a series component, a parallel component, a combination of series or parallel components, or a combination of series and parallel components.

A further embodiment of the present invention includes active components used on the receive side of an imaging system. This active circuitry can include a negative capacitance on the receive side that can balance the electrostatic transducer capacitance. This embodiment can be used alone, or in combination with, other embodiments of the present invention, such as, the balancing transmit and/or receive reactance.

Figure 6:
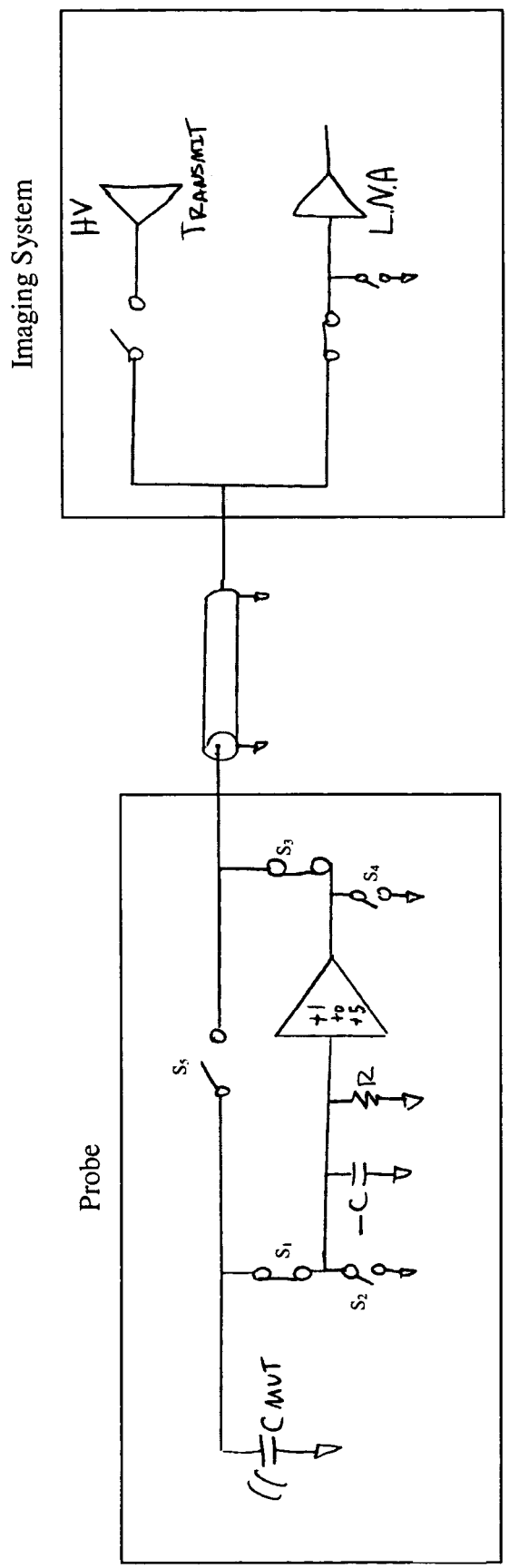
FIG. 6 illustrates an exemplary block diagram of the full system incorporating at least one embodiment of the present invention.

FIG. 6 illustrates an exemplary block diagram of the full system incorporating at least one embodiment of the present invention, including the ultrasonic imaging system front end for one of many channels (e.g., 192 total channels), the probe for one of many channels and the interconnection between the probe and the imaging system (e.g., a coax). As shown in FIG. 6, this embodiment can include the following items in the probe: negative capacitance, high voltage switches and a low noise amplifier (LNA). Switches $S_1$ and $S_3$ can protect the negative capacitor and amplifier during transmit. Switch $S_5$ can connect the transmit path to the transducer, a cMUT as shown, and then break the positive feedback path during receive. Switches $S_2$ and $S_4$ can ground leakage current during the high voltage transmit to help speed amplifier recovery. It is important to note, for example, that in this embodiment at least switches must be high voltage switches.

Figure 7:
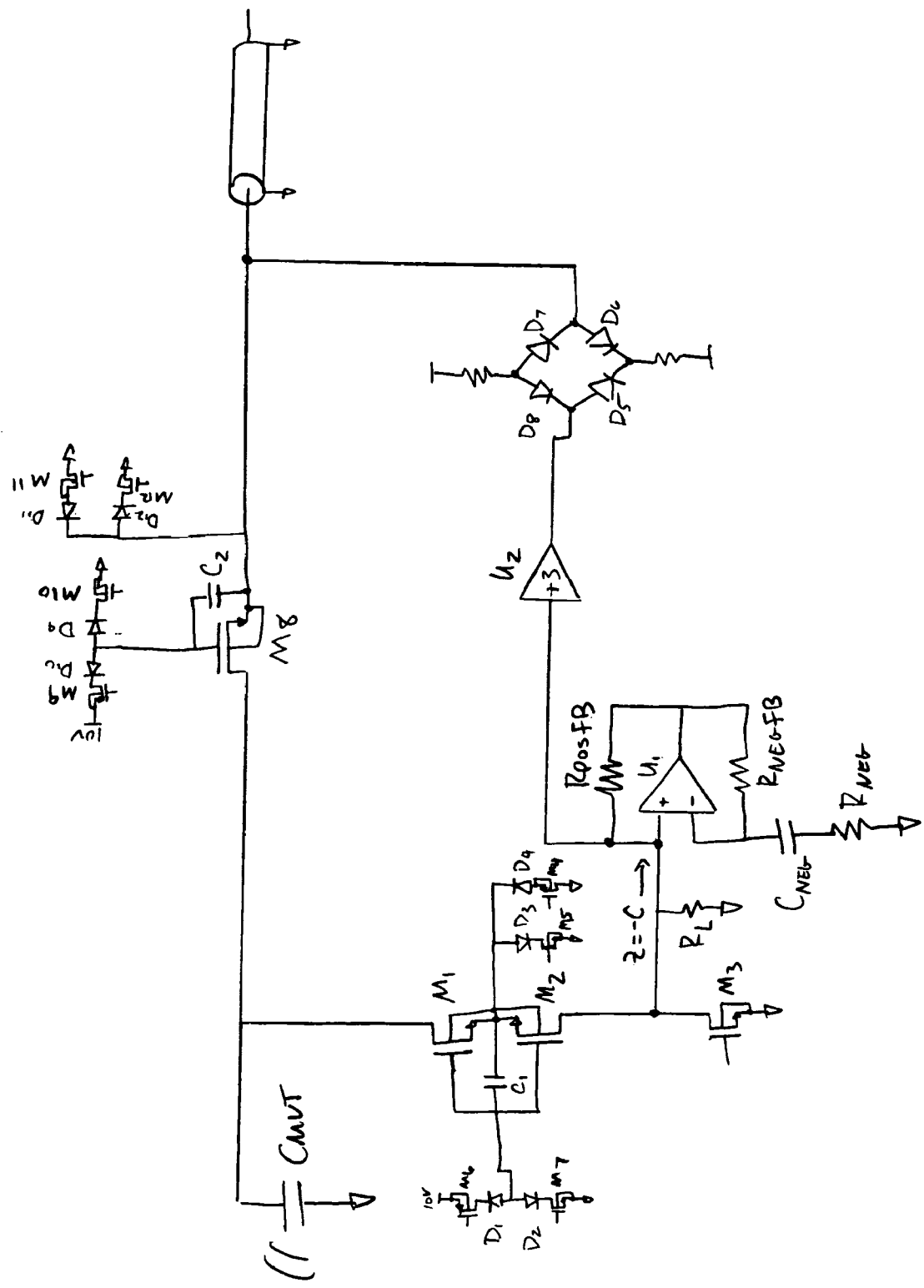
FIG. 7 illustrates a detailed schematic of a negative capacitance probe according to an embodiment of the present invention.

FIG. 7 illustrates a detailed schematic of a negative capacitance probe according to an embodiment of the present invention. As shown in the circuit of FIG. 7, there are 12 transistors, of which two, $M_1$ and $M_2$, are high voltage and low $R_{DSON}$ FETs. Of the remaining transistors, $M_4$-$M_7$ and $M_9$-$M_{12}$ will see +/−transmit voltage (e.g., PFETs would see −100 v, NFETs would see +100 v) but can switch slowly, therefore they can be smaller, high $R_{DSON}$ FETs, and $M_8$ will not see high voltage, since it is on when the transmit pulse comes. $M_8$ can be low $R_{DSON}$, but since it is not high voltage, there are no design problems associated with it. Thus, the high area devices in this embodiment are transistors $M_1$ and $M_2$, which form a load switch to protect $U_1$ against bipolar transmit pulses. These devices are both high voltage and low $R_{DSON}$, for example, on the order of 10Ω or less. Note that these devices will see approximately +/−transmit voltage (e.g., +/−100 v) across them, not the full 200 v bipolar swing.

As further shown in the embodiment of FIG. 7, $U_1$ represents the negative capacitance, here implemented using an op-amp. $U_2$ is a simple low gain LNA. $D_5$ through $D_8$ represent a passive high voltage protection circuit, which can be too high in series impedance to be used in place of $M_1$ and $M_2$.

In operation, the circuit of FIG. 7, when used with the system of FIG. 6, can perform, per at least one embodiment of the present invention, under the following conditions. The transmit voltage can be on the order of plus or minus 100 V, with a 2-cycle, 10 MHz transmit waveform (e.g., sine wave, square wave, etc.). The M1/M2 T/R switch resistance might be less than about 5Ω, but can be canceled completely by the negative capacitor circuit. The receive path recovery time can be less than approximately 500 nanoseconds (nsec). The dynamic range of the LNA might be about 70 dB from approximately 100 mV down to approximately 20 μV. The LNA gain can be small, on the order of about 1 to about 5, to meet the dynamic range parameter, with a maximum output voltage of less than about 200 mV (i.e., which is significantly less than the $V_T$ drop of a silicon diode). The power required by such a circuit can be less than approximately 1 mA per channel. However, if higher power requirements are used, the circuits can be cooled, for example, by water or other suitable cooling means. A complete probe package might be, for example, with 192 channels, produced on a single silicon die that is approximately 40 mm$^2$ in size.

Figure 8:
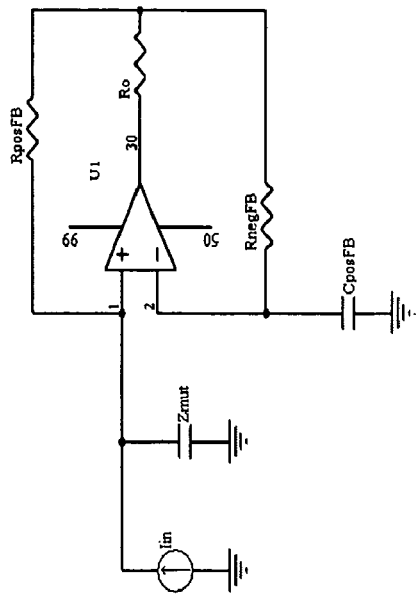
FIG. 8 illustrates two types of negative capacitor circuits using op-amps according to embodiments of the present invention.
Figure 8:
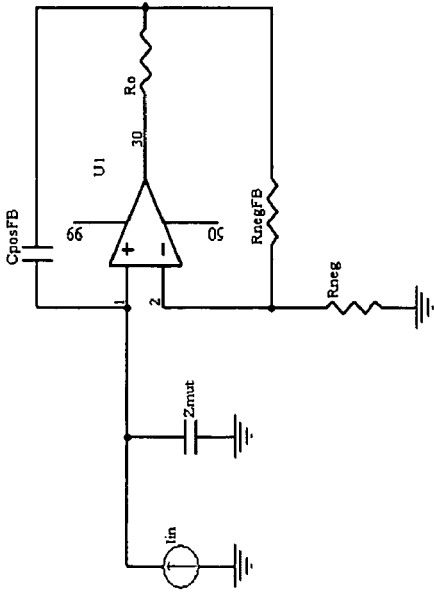
Figure 9:
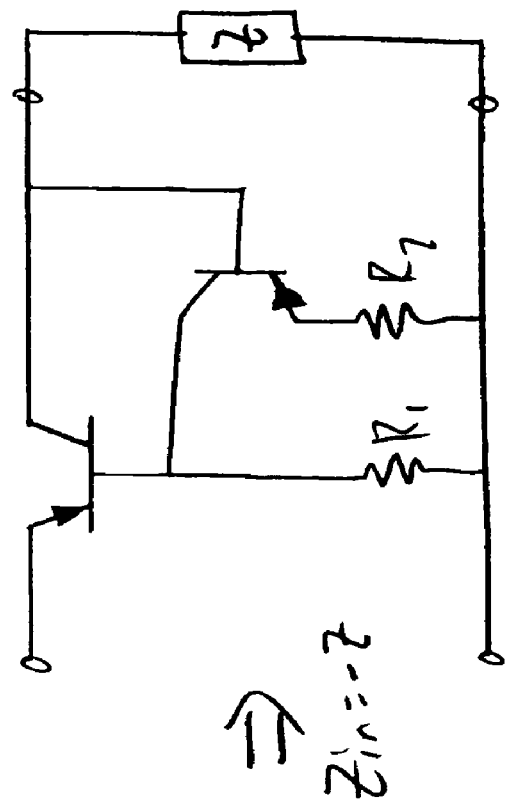
FIG. 9 illustrates two exemplary 2-transistor negative capacitor circuits according to aspects of the present invention.
Figure 9:
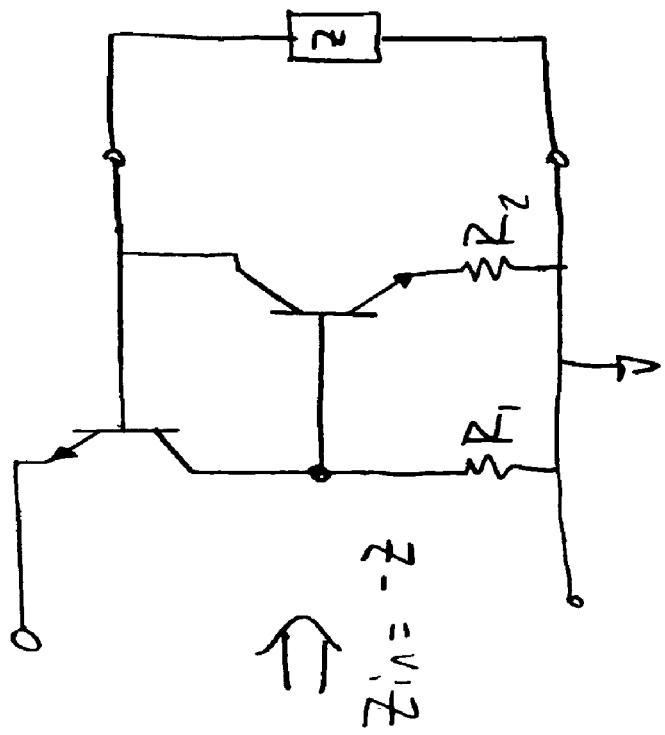

FIG. 8 illustrates two types of negative capacitor circuits using op-amps according to embodiments of the present invention. Both of these two types are presented in simple form and in complete form (i.e., with parasitic elements shown). While the present invention can at least incorporate either type of circuit shown in FIG. 8, this disclosure will primarily focus on the exemplary Type 1 negative capacitor, without limitation to it. As for the circuits of FIG. 8, the operation of the negative capacitor is actually quite simple. By way of illustration, in the Type 2 circuit, the + and − terminals are held at the same potential. The current through RnegFB is mirrored back through RposFB. Since the current is coming out of the RposFB, instead of into RposFB, the current is negative. Hence the impedance is $V/(-I)=-Z$. This $-Z$ is illustrated on FIG. 8, for example, as $Z=-C$. It is further possible to build negative capacitors out of simple 2-transistor circuits. FIG. 9 illustrates two exemplary 2-transistor negative capacitor circuits according to aspects of the present invention.

Figure 10A:
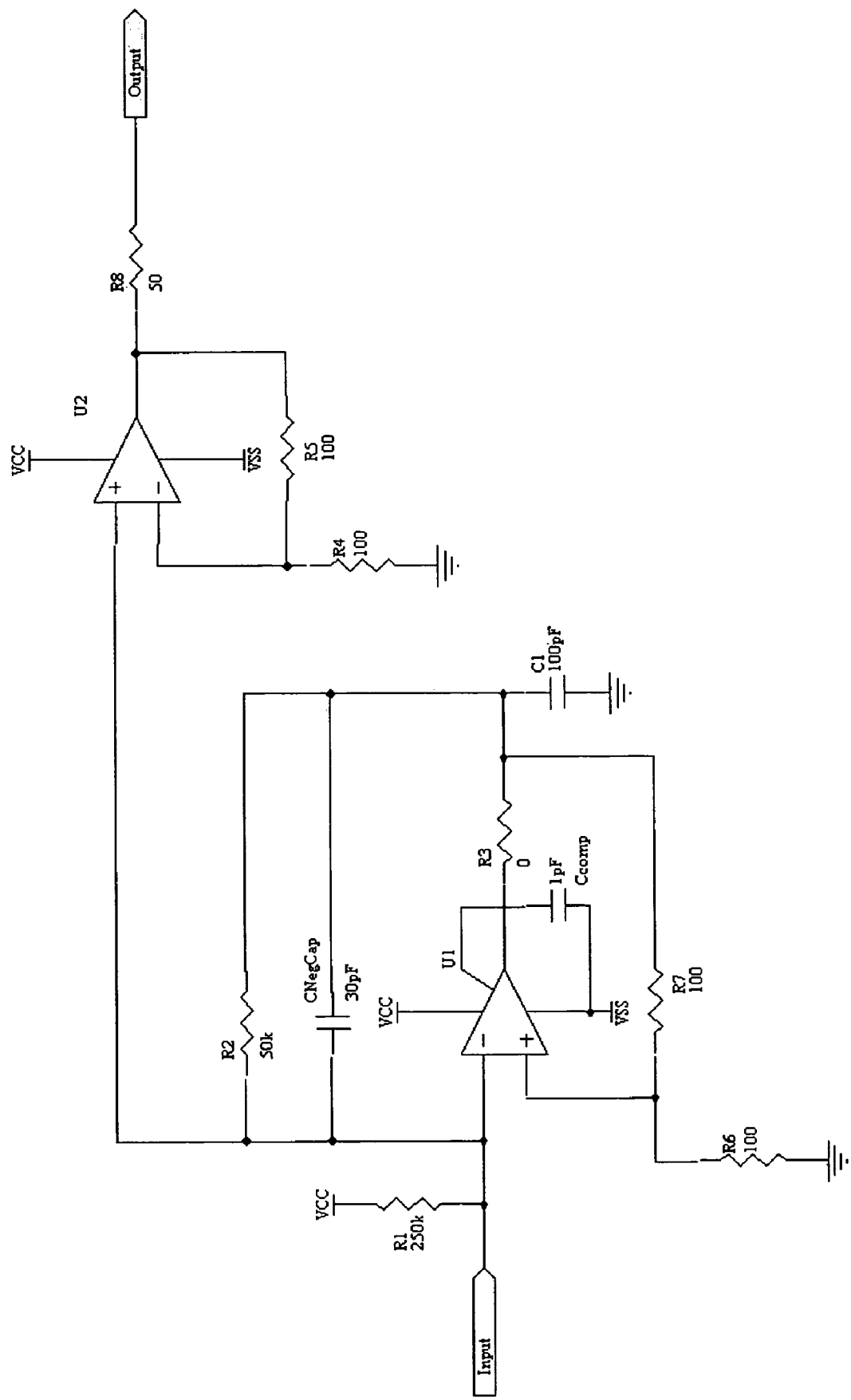
FIGS. 10A-10B illustrate one exemplary Type 1 negative capacitor according to one or more embodiments of the present invention.
Figure 10B:
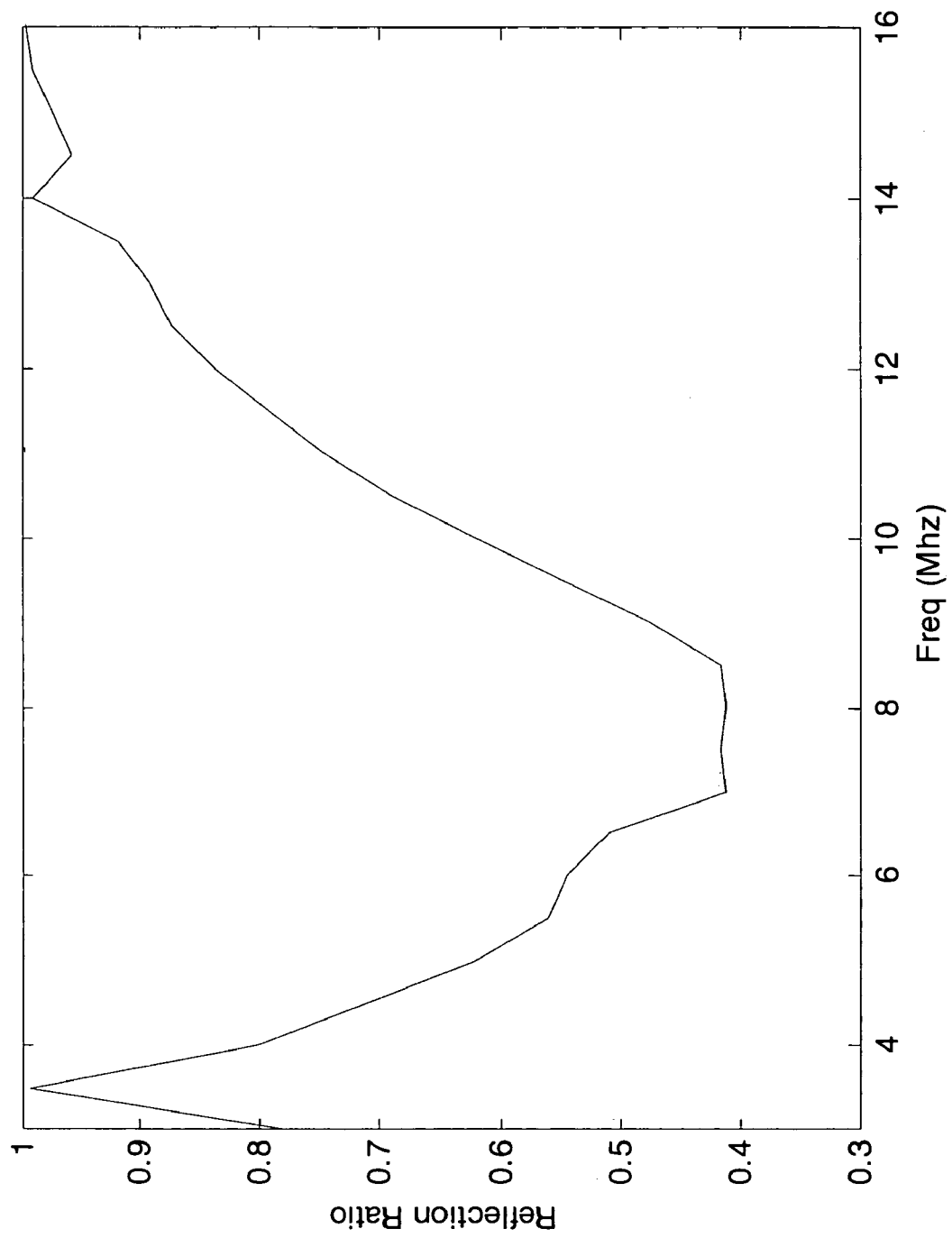

One exemplary Type 1 negative capacitor according to one or more embodiments of the present invention has been built and tested in the laboratory by the inventors. The circuit is depicted in FIG. 10A, with FIG. 10B illustrating the effect of the circuit on the reflectivity of an acoustic wave that impinges on the surface of the receiving MUT. Depicted in FIG. 10B is the ratio of the reflectivity at the surface with the active negative capacitor circuit inserted into the receive path of a typical 8 MHz center frequency capacitive transducer versus the reflectivity without the balancing negative capacitor. Further optimization is possible, as may be evident to those skilled in the art in light of this disclosure, but FIG. 10B is the first laboratory demonstration of one aspect of the present invention.

Figure 11:
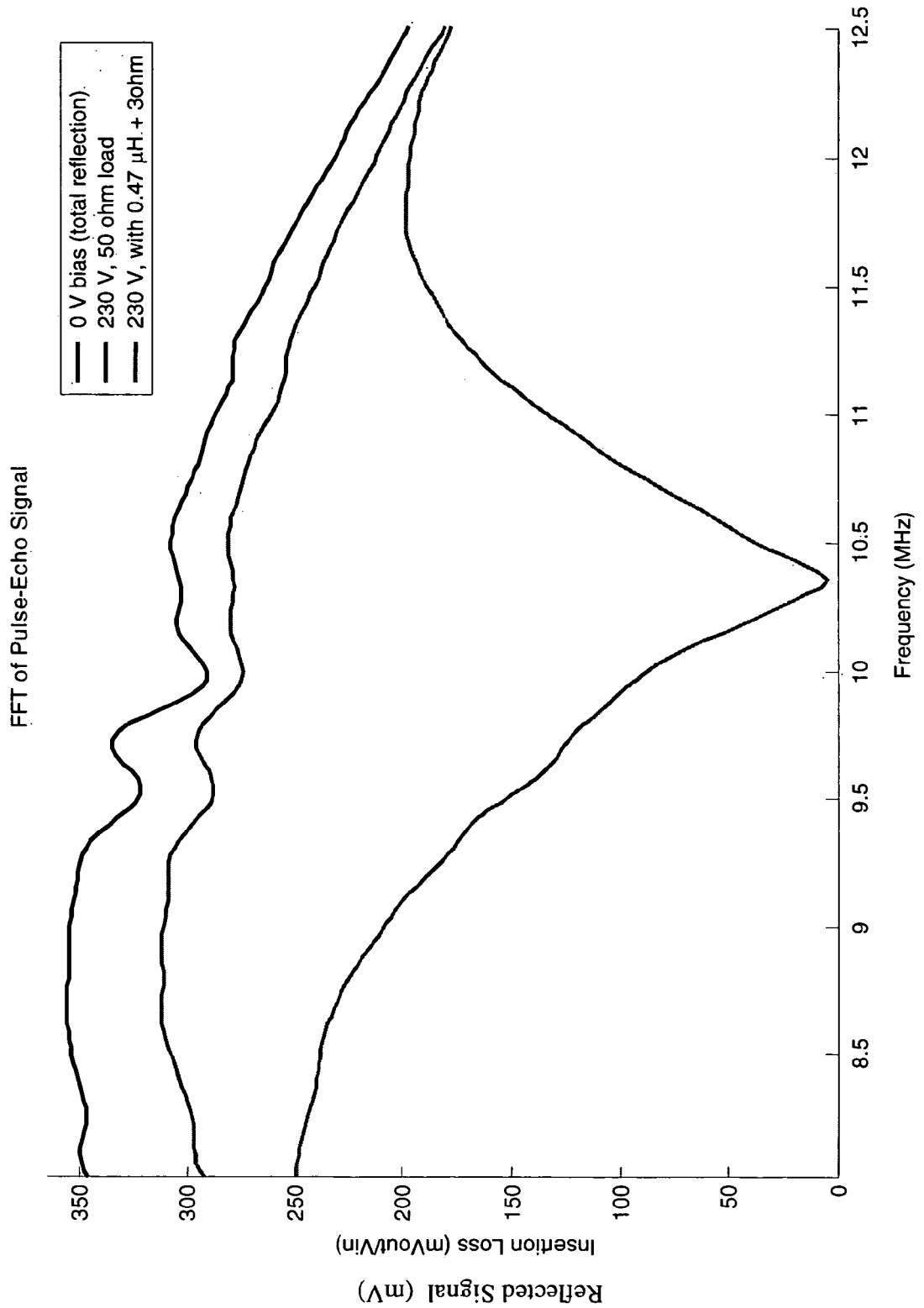
FIG. 11 illustrates the effect on transducer reflectivity of placing an inductor in the receive path of a capacitive microfabricated transducer circuit according to an embodiment of the present invention.

Passive inductive tuning has also been validated in the laboratory. FIG. 11 illustrates the effect on transducer reflectivity of placing an inductor in the receive path of a capacitive microfabricated transducer circuit. The data shown corresponds to a 2.8 mm circular transducer with device capacitance, including parasitic capacitances, of 550 pF, and a real to imaginary ratio at the center frequency of 10.3 MHz of approximately 1:10. By inserting a 0.47 microHenry inductor, a 3 Ohm resistor, and a 50 nF blocking capacitor, all in series shunting the MUT, the significant improvement in reflectivity shown in FIG. 11 was obtained.

Figure 12:
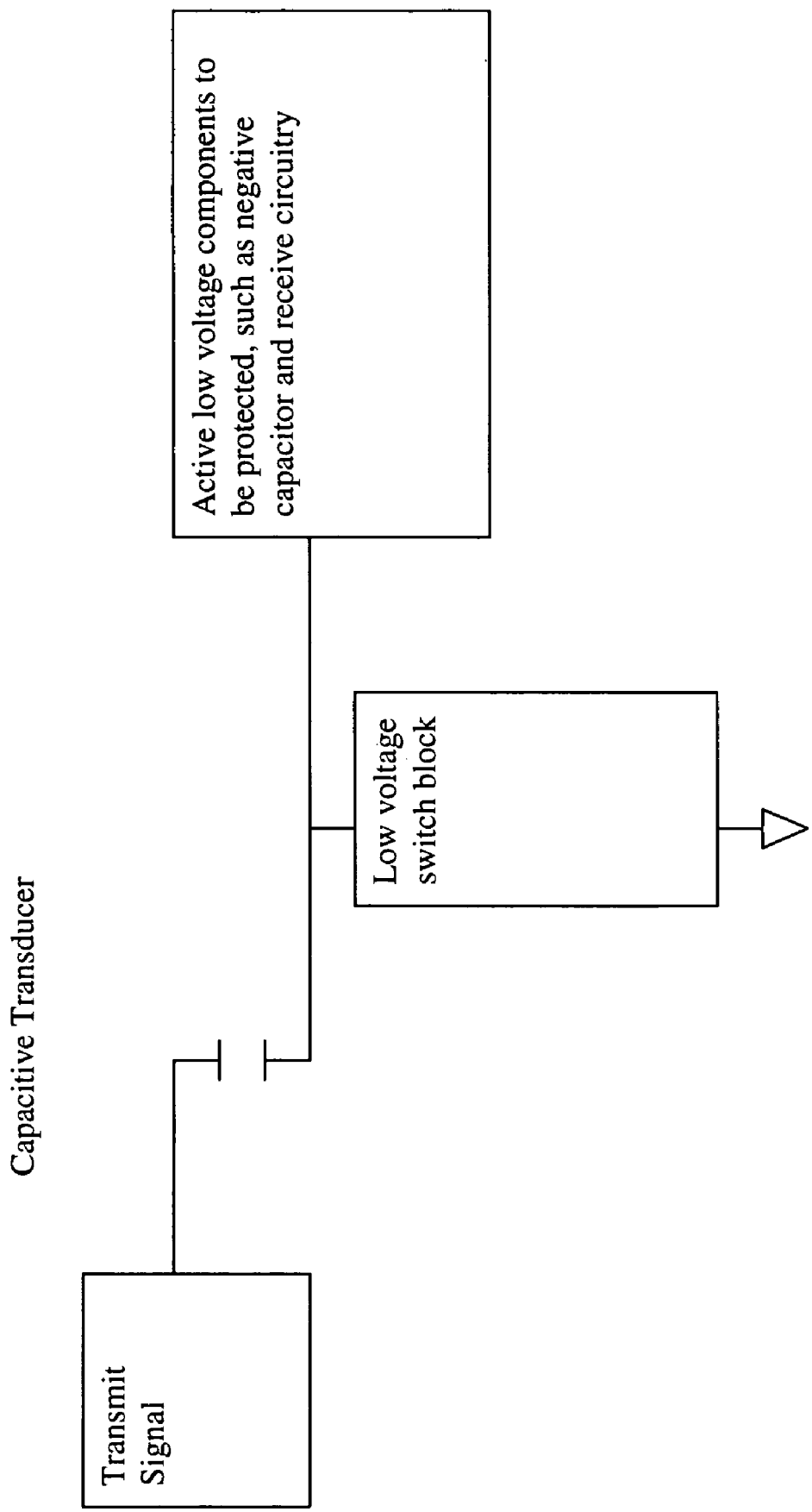
FIG. 12 illustrates a circuit topology whereby a large transmit signal is applied to one electrode of the capacitive transducer and the receive signal is detected from the opposing electrode.

A further embodiment of the present invention provides for receive circuit protection without the need for high voltage electronics. Because it may be desirable to provide an imaging probe of compact size with active elements in the receive path to balance the reactance of the transducer over a broad frequency range, integrated circuit manufacturing processes are desirable. The circuit can be monolithically integrated with the transducer or as part of a multi-chip module, as is known in the art. However, it is difficult to provide both high voltage and low voltage components in a single semiconductor fabrication process. The present inventors have recognized that a circuit topology whereby the large transmit signal is applied to one electrode of the capacitive transducer and the receive signal is detected from the opposing electrode. This topology provides an opportunity to protect the receiving circuitry with low voltage electronics because most of the transmit voltage is dropped across the transducer itself. FIG. 12 demonstrates a block diagram of such a topology, where FIG. 3B shows a diode embodiment for the switching block, though equivalent implementations known to those skilled in the art in light of this disclosure, such as transistor switches, can be used as well.

Figure 13A:
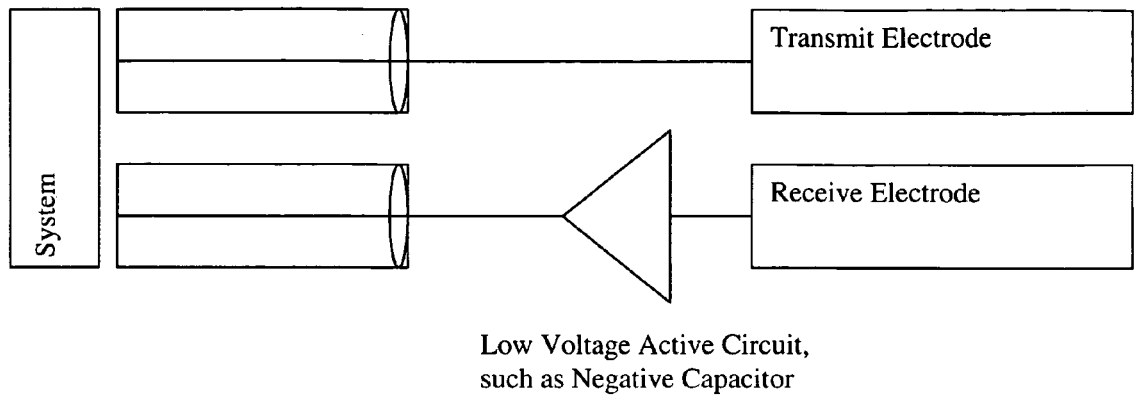
FIGS. 13A-13B illustrate probe systems using two connectors per channel and one connector per channel that incorporate aspects of the present invention.
Figure 13B:
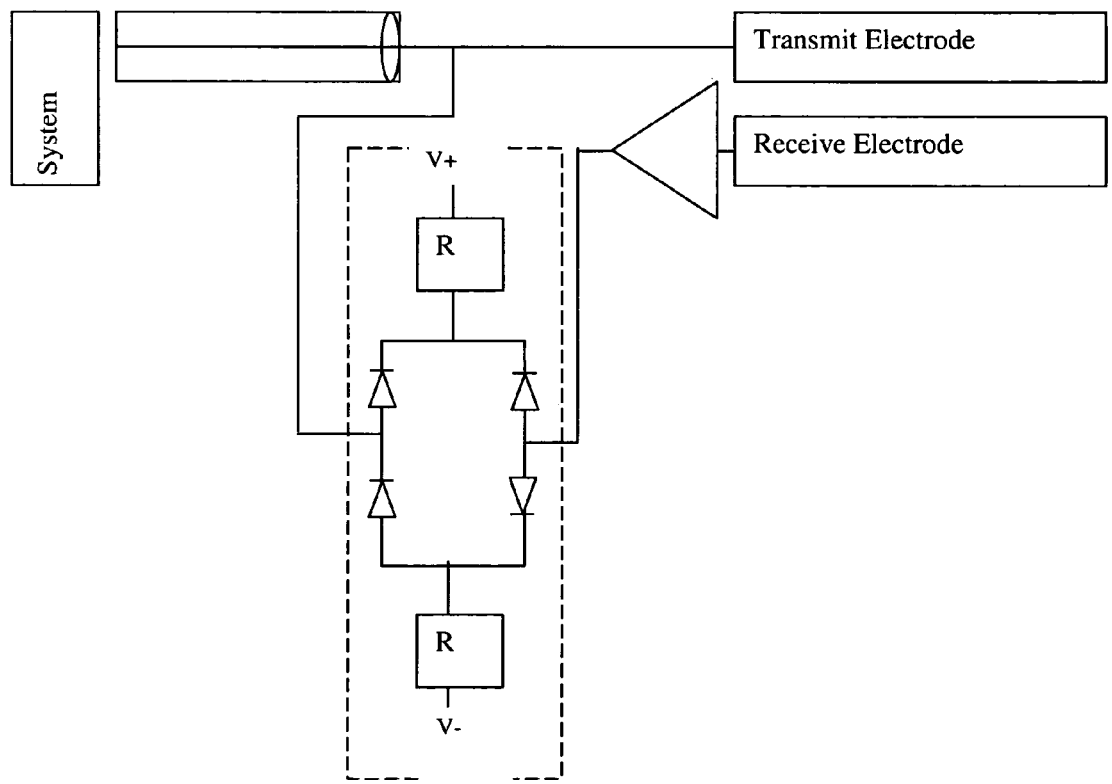

In the case of a two connector per channel system, one channel of which is shown in FIG. 13A, simply separating the transmit and receive electrodes is sufficient. However, most existing ultrasound systems are based on a single connector per channel. In this case, a high voltage switch block is necessary to enable a single cable to carry both the transmit and the receive signals. An embodiment that enables this approach is illustrated in FIG. 13B, where a diode bridge switch is used. Other switch topologies known in the art can also be used.

Figure 14A:
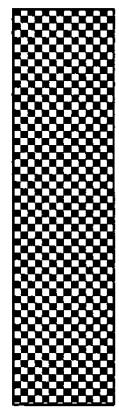
FIGS. 14A-14B illustrate probe systems using two electrode sets formed on the same side of the transducer cells according to at least one embodiment of the present invention.
Figure 14B:
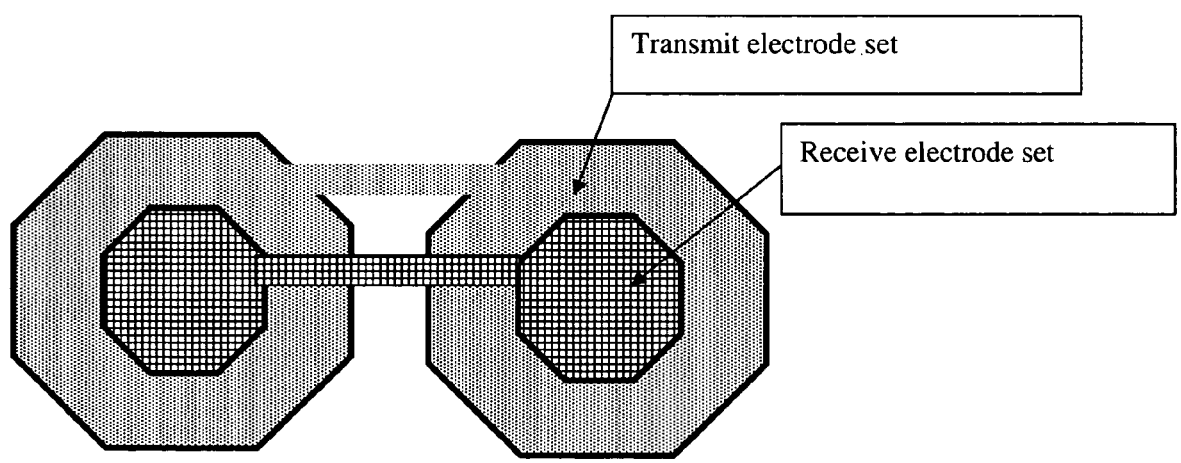

In another embodiment of the present invention, it is not necessary to split the transmit and receive connections between opposing electrodes of the transducer. Rather, two electrode sets formed on the same side of the transducer cells can be used, where a first electrode set connects to a transmit transducer cell subset, and where a second electrode set connects to a receiver transducer cell subset. FIG. 14A illustrates a transducer array according to the two electrode sets of this embodiment where the two subsets are interleaved in a checkerboard pattern, but other distributions are within the scope of the invention. FIG. 14B illustrates an embodiment of the present invention where each cell contains a transmit and a receive electrode on the same side of the capacitive transducer cells. These electrodes can be, for example, produced in different layers of the device. Because cancellation of reactance is possible in accordance with the present invention, the splitting of available electrode area into transmit and receive sub-sets of each transducer cell is not detrimental. Further still, as taught by Ladabaum in U.S. Pat. No. 6,271,620, the central part of the transducer cell is a desirable location for electrode placement to maximize receive sensitivity; the remaining area can be used for transmit electrode placement.

Although the present invention has been particularly described with reference to embodiments thereof, it should be readily apparent to those of ordinary skill in the art that various changes, modifications and substitutes are intended within the form and details thereof, without departing from the spirit and scope of the invention. Accordingly, it will be appreciated that in numerous instances some features of the invention will be employed without a corresponding use of other features. Further, those skilled in the art will understand that variations can be made in the number and arrangement of components illustrated in the above figures. It is intended that the scope of the appended claims include such changes and modifications.

What is claimed is:

1. A method of tuning a transducer circuit comprising the steps of:

providing the transducer circuit having an ultrasonic transducer that includes at least one reactance characteristic and an operating frequency range, the ultrasonic transducer comprising a capacitive microfabricated electrostatic transducer, and at least one signal path that is electrically coupled to the ultrasonic transducer, the at least one signal path including a receive signal path, the receive signal path receiving an electric receive signal generated with transduction from ultrasound energy by the ultrasonic transducer and outputting the electric receive signal to an imaging system, wherein the at least one signal path further includes a transmit signal path; and inserting a balancing circuit into the at least one signal path to substantially balance the at least one reactance characteristic of the ultrasonic transducer over the operating frequency range, the balancing circuit comprising an active circuit;

wherein the balancing circuit is inserted into the receive signal path.

2. The method of claim 1, wherein the at least one reactance characteristic includes a capacitance of the ultrasonic transducer.

3. The method of claim 1, wherein the balancing circuit includes a negative capacitor circuit to substantially balance the capacitance of the ultrasonic transducer.

4. The method of claim 3, wherein the negative capacitor includes an op-amp and a plurality of feedback resistors.

5. The method of claim 3, wherein the negative capacitor includes a pair of transistors.

6. The method of claim 3, wherein the balancing circuit further includes a plurality of switches to isolate the balancing circuit from the ultrasonic transducer during a transmission.

7. The method of claim 6, wherein the plurality of switches include a plurality of transistors.

8. The method of claim 6, wherein the at least one reactance characteristic further includes a negative reactance of the ultrasonic transducer.

9. The method of claim 8, wherein the balancing circuit further includes an inductance for substantially balancing the negative reactance of the ultrasonic transducer over the frequency range, the inductance being inserted into the transmit signal path and isolated from the receive signal path during the transmission using the plurality of switches.

10. The method of claim 1, wherein:
the transmit signal path of the transducer circuit is electrically coupled to the ultrasonic transducer using a first electrode of the ultrasonic transducer; and
the receive signal path of the transducer circuit is electrically coupled to the ultrasonic transducer using a second electrode of the ultrasonic transducer.

11. The method of claim 10, wherein the first electrode is a high voltage signal path and the second electrode is a low voltage signal path.

12. The method of claim 11, wherein the balancing circuit includes a negative capacitor circuit that is inserted into the low voltage signal path for substantially balancing the at least one reactance characteristic.

13. The method of claim 12, wherein the balancing circuit further includes an inductance that is inserted into the high voltage signal path for further substantially balancing the at least one reactance characteristic.

14. A tuned transducer circuit comprising:
an electro-acoustic transducer circuit having an ultrasonic transducer that includes at least one reactance characteristic and an operating frequency range, and at least one signal path that is electrically coupled to the ultrasonic transducer, the at least one signal path including a receive signal path for reception of electrical signals representing ultrasound echoes; and a balancing circuit that is inserted into the at least one signal path to substantially balance the at least one reactance characteristic of the ultrasonic transducer over the operating frequency range, wherein the balancing circuit is inserted into the receive signal path.

15. The circuit of claim 14, wherein the at least one signal path further includes a transmit signal path.

16. The circuit of claim 15, wherein the at least one reactance characteristic includes a capacitance of the ultrasonic transducer.

17. The method of claim 15, wherein:
the transmit signal path of the transducer circuit is electrically coupled to the ultrasonic transducer using a first electrode of the ultrasonic transducer; and
the receive signal path of the transducer circuit is electrically coupled to the ultrasonic transducer using a second electrode of the ultrasonic transducer.

18. The method of claim 17, wherein the first electrode is a high voltage signal path and the second electrode is a low voltage signal path.

19. The method of claim 18, wherein the balancing circuit includes a negative capacitor circuit that is inserted into the low voltage signal path for substantially balancing the at least one reactance characteristic.

20. The method of claim 19, wherein the balancing circuit further includes an inductance that is inserted into the high voltage signal path for further substantially balancing the at least one reactance characteristic.

21. The circuit of claim 14, wherein the balancing circuit includes a negative capacitor circuit to substantially balance the capacitance of the ultrasonic transducer.

22. The circuit of claim 21, wherein the negative capacitor includes a pair of transistors.

23. The circuit of claim 21, wherein the negative capacitor includes an op-amp and a plurality of feedback resistors.

24. The circuit of claim 23, wherein the balancing circuit further includes an inductance for substantially balancing the negative reactance of the ultrasonic transducer over the operating frequency range, the inductance being inserted into the transmit signal path and isolated from the receive signal path during the transmission using the plurality of switches.

25. The circuit of claim 21, wherein the balancing circuit further includes a plurality of switches to isolate the balancing circuit from the ultrasonic transducer during a transmission.

26. The circuit of claim 25, wherein the plurality of switches include a plurality of transistors.

27. The circuit of claim 25, wherein the at least one reactance characteristic further includes a negative reactance of the ultrasonic transducer.

28. A method of tuning a transducer circuit comprising the steps of:
providing the transducer circuit having an ultrasonic transducer that includes a capacitance and an operating frequency range, and a receive signal path that is electrically coupled to the ultrasonic transducer for reception of electrical signals representing ultrasound echoes;
inserting a negative capacitor into the receive signal path to substantially balance the capacitance of the ultrasonic transducer over the operating frequency range; and
isolating the negative capacitor from the ultrasonic transducer during a transmission of the transducer circuit using a plurality of switches.

29. The method of claim 28, wherein the ultrasonic transducer further includes a negative reactance and a transmit signal path, and the balancing circuit further includes an inductance for substantially balancing the negative reactance of the ultrasonic transducer over the operating frequency range, the inductance being inserted into the transmit signal path and isolated from the receive signal path during the transmission using the plurality of switches.

30. A tuned transducer circuit comprising:
a transducer circuit having an ultrasonic transducer that includes a capacitance and an operating frequency range, the ultrasonic transducer comprising a capacitive microfabricated electrostatic transducer, and a receive signal path that is electrically coupled to the ultrasonic transducer, the receive signal path receiving an electric receive signal generated with transduction from ultrasound energy by the ultrasonic transducer and outputting the electric receive signal to an imaging system;
a negative capacitor inserted into the receive signal path to substantially balance the capacitance of the ultrasonic transducer over the operating frequency range; and a plurality of switches that isolate the negative capacitor from the ultrasonic transducer during a transmission of the transducer circuit.

31. The circuit of claim 30, wherein the ultrasonic transducer further includes a negative reactance and a transmit signal path, and the balancing circuit further includes an inductance for substantially balancing the negative reactance of the ultrasonic transducer over the operating frequency range, the inductance being inserted into the transmit signal path and isolated from the receive signal path during the transmission using the plurality of switches.

32. A method of tuning a transducer circuit comprising the steps of:
providing the transducer circuit having a plurality of ultrasonic transducers, each ultrasonic transducer including a capacitance and an operating frequency range, the ultrasonic transducers comprising capacitive microfabricated electrostatic transducers, and one or more receive signal paths that are electrically coupled to the plurality of ultrasonic transducers the receive signal paths each receiving an electric receive signal generated with transduction from ultrasound energy by respective ultrasonic transducers and outputting the electric receive signals to an imaging system;
inserting a balancing circuit into the one or more receive signal paths to substantially balance the capacitance of each ultrasonic transducer over the operating frequency range; and isolating the balancing circuit from the plurality of ultrasonic transducers during a transmission of the transducer circuit using a plurality of switches.

33. The method of claim 32, wherein the balancing circuit is a negative capacitor.

34. The method of claim 32, wherein each ultrasonic transducer further includes a negative reactance and one or more transmit signal paths, and the balancing circuit further includes an inductance for substantially balancing the negative reactance of the ultrasonic transducer over the operating frequency range, the inductance being inserted into the one or more transmit signal paths and isolated from the one or more receive signal paths during the transmission using the plurality of switches.

35. A tuned transducer circuit comprising:
a transducer circuit having a plurality of ultrasonic transducers, each ultrasonic transducer including a capacitance and an operating frequency range, the ultrasonic transducers comprising capacitive microfabricated electrostatic transducers, and one or more receive signal paths that are electrically coupled to the plurality of ultrasonic transducers, the receive signal path receiving an electric receive signal generated with transduction from ultrasound energy by the ultrasonic transducer and outputting the electric receive signal to an imaging system;
a balancing circuit inserted into the one or more receive signal paths to substantially balance the capacitance of each ultrasonic transducer over the operating frequency range the balancing circuit comprising an active circuit; and
a plurality of switches that isolate the balancing circuit from the plurality of ultrasonic transducers during a transmission of the transducer circuit.

36. The circuit of claim 35, wherein the balancing circuit is a negative capacitor.

37. The circuit of claim 35, wherein each ultrasonic transducer further includes a negative reactance and one or more transmit signal paths, and the balancing circuit further includes an inductance for substantially balancing the negative reactance of the ultrasonic transducer over the operating frequency range, the inductance being inserted into the one or more transmit signal paths and isolated from the one or more receive signal paths during the transmission using the plurality of switches.

* * * * *